(12) United States Patent
Smith et al.

(10) Patent No.: US 8,240,009 B2
(45) Date of Patent: *Aug. 14, 2012

(54) NON-WOVEN FIBER ASSEMBLIES

(75) Inventors: Daniel J. Smith, Stow, OH (US);
Darrell H. Reneker, Akron, OH (US)

(73) Assignee: The University Of Akron, Akron ( * ) Notice: Subject to any disclaimer, the term of this patent is extended or adjusted under 35 U.S.C. 154(b) by 108 days.

This patent is subject to a terminal disclaimer.

(21) Appl. No.: 12/829,976

(22) Filed: Jul. 2, 2010

(65) Prior Publication Data

US 2011/0028878 A1    Feb. 3, 2011

Related U.S. Application Data

(63) Continuation of application No. 10/510,457, filed as application No. PCT/US03/10652 on Apr. 4, 2003, now Pat. No. 7,765,647.

(60) Provisional application No. 60/370,051, filed on Apr. 4, 2002.

(51) Int. Cl.
*D01G 13/00* (2006.01)

(52) U.S. Cl. .......................................... 19/145; 19/296

(58) Field of Classification Search .................. 19/145, 19/296; 428/373
See application file for complete search history.

(56) References Cited

U.S. PATENT DOCUMENTS

| | | | | |
|---|---|---|---|---|
| 5,238,733 A * | 8/1993 | Joseph et al. | | 442/151 |
| 5,352,216 A * | 10/1994 | Shiono et al. | | 604/312 |
| 6,114,024 A * | 9/2000 | Forte | | 428/315.9 |
| 6,753,454 B1 * | 6/2004 | Smith et al. | | 602/41 |
| 7,765,647 B2 * | 8/2010 | Smith et al. | | 19/145 |
| 2001/0018123 A1 * | 8/2001 | Furumori et al. | | 428/343 |
| 2003/0186051 A1 * | 10/2003 | Figuly et al. | | 428/373 |

OTHER PUBLICATIONS http://www.kbseiren.com/english/pro-esp.html, 2007, ESPANSIONE.*

* cited by examiner

*Primary Examiner* — Shaun R Hurley
(74) *Attorney, Agent, or Firm* — Renner Kenner Greive Bobak Taylor & Weber

(57) ABSTRACT

In one embodiment, the present invention relates to a non-woven fiber assembly comprising one or more fibers wherein each fiber contains: a hydrophilic component; and an elastomeric component, and wherein the non-woven fiber assembly further comprises an adhesive component. In still another embodiment, the present invention relates to a non-woven fiber assembly comprising one or more fibers wherein each fiber contains: a hydrophilic component; an elastomeric component; and an adhesive component, wherein the hydrophilic component, the elastomeric component and the adhesive component are all contained within each fiber. Also disclosed is a method of making the afore-mentioned non-woven fiber assemblies. Additionally, a medical dressing made from the non-woven fiber assemblies of the present invention is disclosed.

16 Claims, 2 Drawing Sheets

NON-WOVEN FIBER ASSEMBLIES

RELATED APPLICATION DATA

This application claims is a continuation of and claims priority to U.S. patent application Ser. No. 10/510,457, filed Jul. 25, 2005, which is a 35 U.S.C. §371 application of PCT/US2003/10652, filed Apr. 4, 2003, which claims priority to U.S. Provisional Patent Application No. 60/370,051, filed Apr. 4, 2002, the entireties of which are hereby incorporated herein by reference.

BACKGROUND OF THE INVENTION

This invention relates to composite fiber assemblies. More particularly, this invention relates to composite nanofiber assemblies that can be produced from a polymeric matrix material.

Various techniques are known in the textile field for the creation of fibers. Melt-blowing, the nanofibers by gas jet (NGJ) technique, and electrospinning are included among these techniques. In a melt-blowing process, a stream of molten polymer or other fiber-forming material is typically extruded into a jet of gas to form fibers. The resulting fibers are typically greater than 1,000 nanometers in diameter, and more typically, greater than 10,000 nanometers in diameter.

A technique and apparatus for forming fibers having a diameter of less than 3,000 nanometers according to the NGJ technique is described in U.S. Pat. Nos. 6,382,526 and 6,520,425, the disclosures of which are hereby incorporated by reference.

The electrospinning of liquids and/or solutions capable of forming fibers, also known within the fiber forming industry as electrostatic spinning, is well known and has been described in a number of patents as well as in the general literature. The process of electrospinning generally involves the creation of an electrical field at the surface of a liquid. The resulting electrical forces create a jet of liquid that carries electrical charge. Thus, the liquid jets may be attracted to other electrically charged objects at a suitable electrical potential. As the jet of liquid elongates and travels, it will harden and dry. The hardening and drying of the elongated jet of liquid may be caused by cooling of the liquid, i.e., where the liquid is normally a solid at room temperature; evaporation of a solvent, e.g., by dehydration, (physically induced hardening); or by a curing mechanism (chemically induced hardening). The produced fibers are collected on a suitably located, oppositely charged receiver and subsequently removed from it as needed, or directly applied to an oppositely charged or grounded generalized target area.

Fibers produced by this process have been used in a wide variety of applications, and are known, from U.S. Pat. No. 4,043,331 to be particularly useful in forming non-woven mats suitable for use in wound dressings. One of the major advantages of using electrospun fibers in wound dressings, is that very thin fibers can be produced having diameters, usually on the order of about 50 nanometers to about 25 microns, and more preferably, on the order of about 50 nanometers to about 5 microns. These fibers can be collected and formed into non-woven mats of any desired shape and thickness. It will be appreciated that, because of the very small diameter of the fibers, a mat with very small interstices and high surface area per unit mass, two characteristics that are important in determining the porosity of the mat, can be produced.

Medical dressings formed using non-woven mats of these polymeric fibers may provide particular benefits depending upon the type of polymer or polymers used, as taught by U.S. Pat. No. 4,043,331. A wettable, or hydrophilic, polymer, such as, for example, a polyurethane may be used, or a non-wetting, or at least weakly hydrophobic, polymer such as, for example, a saturated polyester, may be employed. Where the dressing is formed from a wettable polymer, blood or serum escaping from the wound tends to penetrate the dressing and the high surface area encourages clotting. Such dressings could be used as emergency dressings to halt bleeding. On the other hand, where the dressing is formed from a non-wetting polymer, and if the interstices between the fibers are sufficiently small, i.e., on the order of less than about 100 nanometers, tissue fluids, including blood, tend not to permeate the dressing. Consequently, the fluids are retained adjacent to the wound where clotting will occur. Subsequent removal of such a dressing is facilitated by the absence of blood clots permeating the dressing material. Still further, U.S. Pat. No. 4,043,331 suggests that such dressings have the advantage that they are usually sufficiently porous to allow interchange of oxygen and water vapor between the atmosphere and the surface of the wound.

Besides providing variability as to the diameter of the fibers or the shape, thickness, or porosity of any non-woven mat produced therefrom, the ability to electrospin the fibers also allows for controlled variations in the composition of the fibers, their density of deposition and their inherent strength. The above-identified U.S. patent indicates that it is also possible to post-treat the non-woven mats with other materials to modify their properties. For example, one could increase the strength of the mat using an appropriate binder or increase water resistance by post-treating the mat with silicone or other water-resistant material, such as perfluoro alkyl methacrylate. Alternatively, strength may be increased by utilizing fibers of polytetrafluoroethylene (PTFE).

By varying the composition of the fibers being formed, fibers having different physical or chemical properties may be obtained. This can be accomplished either by spinning a liquid containing a plurality of components, each of which may contribute a desired characteristic to the finished product, or by simultaneously spinning, from multiple liquid sources, fibers of different compositions that are then simultaneously deposited to form a mat. The resulting mat, of course, would consist of intimately intermingled fibers of different material. A further alternative noted in the above-referenced U.S. patent is to produce a mat having a plurality of layers of different fibers of different materials (or fibers of the same material but different characteristics, e.g. diameter), as by, for example, varying the type of fibers being deposited on the receiver over time. For example, wettable and non-wetting polymers each offer additional properties that may be desirable in different applications. Wettable polymers tend to be highly absorbent but provide mats that are relatively weak, while non-wetting polymers tend to be non-absorbent but provide mats that are relatively strong. In some applications, such as medical dressings, for example, it may be desirable to use a combination of wettable and non-wetting polymer layers in a single article. The wettable polymer layer or layers contribute a relatively high level of absorbency to the article while the non-wetting polymer layer or layers contribute a relatively high level of strength. Use of such a laminate-type structure, however, suffers from the disadvantage that the hydrophobic layer can form a barrier to liquids and interfere with the absorption of liquid by the wettable layer. Additionally, upon absorption of liquid, the wettable polymer layer will weaken and misalignment, slipping, or even separation of the layers may occur, resulting in failure of the integrity of the article.

U.S. Pat. No. 4,043,331 indicates that strong, non-woven mats comprising a plurality of fibers of organic, namely polymeric, material may be produced by electrostatically spinning the fibers from a liquid consisting of the material or its precursor. These fibers are collected on a suitably charged receiver. The mats or linings formed on the receiver can then be transferred and used alone or in conjunction with other previously constructed components such as, for example, mats of woven fibers and backing layers to provide a wound dressing of desired characteristics. For instance, in producing wound dressings, additional supports or reinforcement such as mats or linings of fibers, or backing layers may be required in order to adhere the wound dressing to the skin and to provide other desirable properties to the wound dressing. As an example, a mat or lining of woven fibers may contain materials having antiseptic or wound-healing properties. Surface treatments of the already formed non-woven mats may also provide added benefits in the production of such wound dressings. However, U.S. Pat. No. 4,043,331 does not provide a medical dressing that adheres to undamaged skin only. It also does not provide a single-component dressing that can adhere to a desired area of a patient, or a dressing comprised of composite fibers that vary in their composition along their length.

It has also been described in PCT International Publication No. WO98/03267 to electrostatically spin a wound dressing in place over a wound. In such a use, the body itself is grounded and acts as a collector of the electrospun fibers. This method of synthesizing a wound dressing allows for solution of some of the problems associated with bandage and gauze storage and preparation. It is well known for example, that gauze and bandages must be stored and maintained in a sterile environment in order to offer the greatest protection in healing wounds. If the gauze or bandages are not sterile, these products offer little help in protecting the wound. Electrospinning a wound dressing in place, over a wound, from a sterile liquid, eliminates these problems.

Electrospinning a wound dressing in place over a wound, however, limits the types of solvents that may be used to only those solvents that are compatible with the skin or other tissue to which the dressing is applied. Examples of such solvents include water, alcohols, and acetone. Likewise, because the types of usable solvents are limited, the types of additives, such as, for example, absorbents, bactericides, and antibiotics, that may be used in conjunction with the polymer are also limited to those that are soluble, or form a stable dispersion in the particular solvent used. Similarly, the types of polymers that may be used are also limited to those that are soluble in a skin-or tissue-compatible solvent. Biocompatible polymer/solvent combinations include, for example, poly(ethylenimine)/ethanol, poly(vinylpyrrolidone)/ethanol, polyethylene oxide/water, and poly(2-hydroxymethacrylate)/ethanol+ acid. While fibers from such a combination are non-reactive in their state as spun, exposure of the fibers to fluids, either from a wound or from external sources, may cause a local pH change from a neutral or nearly neutral pH to one that is acidic or alkaline, depending on the composition of the fiber. For example, when poly(ethylenimine) fiber is exposed to fluid, it will participate in proton transfer, resulting in an alkaline pH in the fluid contacting the polymer. The creation of an undesirable pH environment may cause side effects, such as slow wound healing.

An electrospun fiber containing a substantially homogeneous mixture of a hydrophilic polymer, a polymer which is at least weakly hydrophobic, and optionally, a pH adjusting compound has been described in International Publication No. WO 01/27365, the disclosure of which is incorporated herein by reference. The fibers may be deposited directly on their intended usage area without first applying the fibers to a transient, charged receiver or subjecting it to other intermediate fabrication steps. The resulting fibers, however, do not provide a dressing which adheres to undamaged skin only.

Therefore, the need continues to exist for a medical dressing or other non-woven mat or membrane that is capable of adhering to a dry substrate but will not adhere to a wet surface such as a wound or to wet tissues that form in the early stages of wound healing. A need also exists for a medical dressing that can provide properties resulting from a variation in the composition of the individual fibers of the dressing over their length.

BRIEF SUMMARY OF THE INVENTION

It is, therefore, an aspect of the present invention to provide a medical dressing or other non-woven mat or membrane that is capable of adhering to a dry substrate such as undamaged skin but will not adhere to a wet substrate such as the surface of a wound or to wet tissues that form in the early stages of wound healing.

It is also an aspect of the present invention to provide a method of making a medical dressing that is capable of adhering to undamaged skin but will not adhere to the wet surface of a wound or to wet tissues that form in the early stages of wound healing.

It is a further aspect of the present invention to provide a medical dressing that contains composite fibers that vary in their composition over their length.

In general, the present invention provides a non-woven fiber assembly comprising one or more fibers, wherein the fibers contain an adhesive component, an elastomeric component and a hydrophilic component.

The present invention also provides a method of making a non-woven fiber assembly. The method comprises the steps of providing at least one fiber-forming material and forming at least one fiber from said at least one fiber-forming material, wherein the at least one fiber forming material comprises an adhesive component, an elastomeric component, and a hydrophilic component.

The present invention also provides a method of treating a patient comprising applying a non-woven fiber assembly to a predetermined area of the patient, wherein the non-woven fiber assembly contains one or more fibers comprising an adhesive component, an elastomeric component, and a hydrophilic component.

The present invention also provides an apparatus for forming at least one composite fiber, the fiber comprising a hydrophilic component, an elastomeric component and an adhesive component, wherein the apparatus comprises a plurality of reservoirs for containing more than one type of fiber-forming material, a plurality of valves, each independently in communication with a reservoir, and a fiber-forming device selected from the group consisting of a spinnerette, a NGJ nozzle, and an electrospinning device, in communication with said valves.

DETAILED DESCRIPTION OF THE INVENTION

Figure 1:
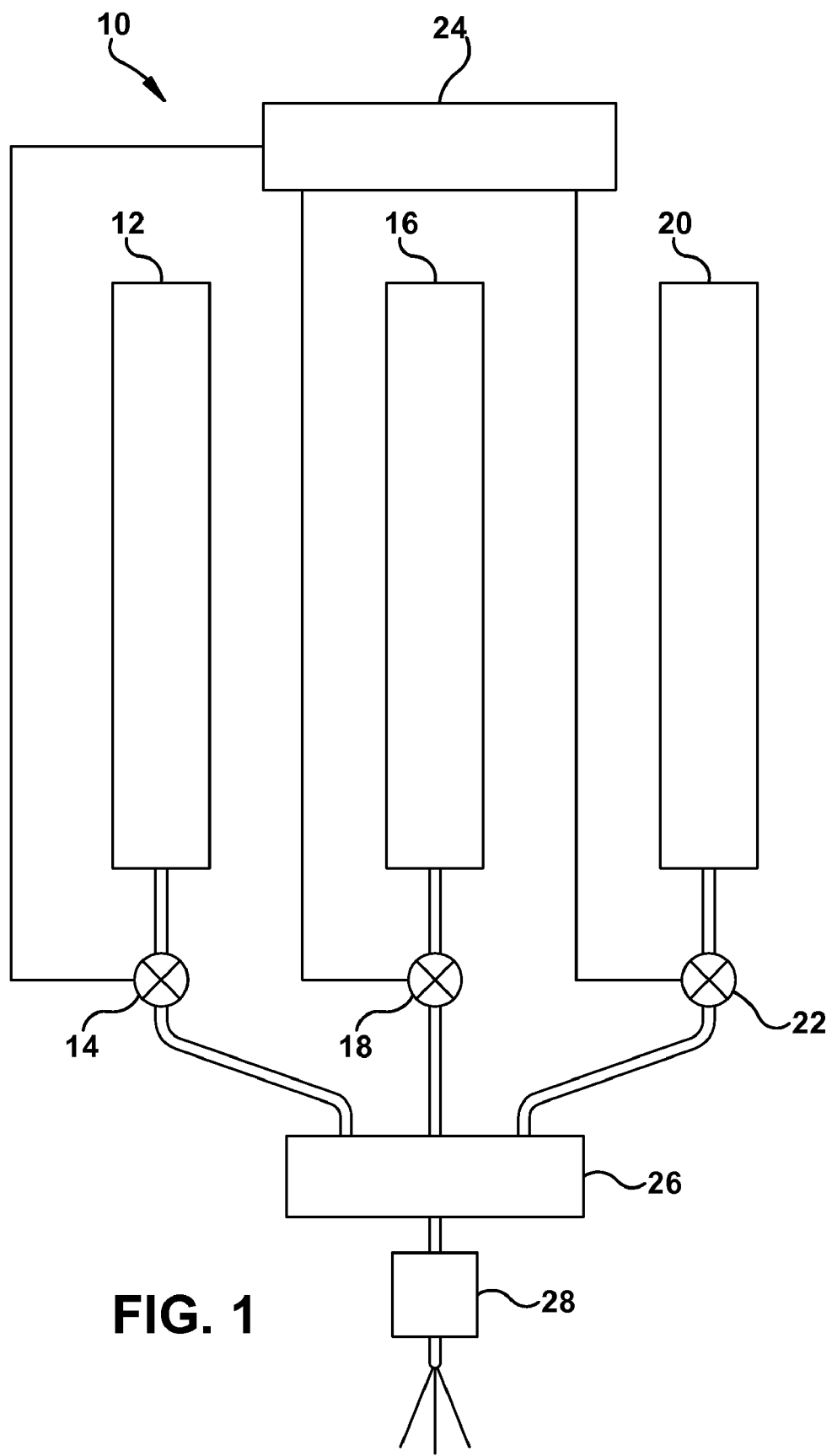
FIG. 1 is a schematic representation of an apparatus for forming composite fibers according to the present invention.

As mentioned above, the present invention provides a non-woven fiber assembly comprising at least one fiber and containing an adhesive component, an elastomeric component, and a hydrophilic component. The at least one fiber may contain a series of segments such as a segment that is primarily or even totally an adhesive component, a segment that is primarily or totally an elastomeric component, and a segment that is primarily or totally a hydrophilic component. When the at least one fiber has such an arrangement of components, the different segments may be arranged in any of a number of orders, depending on the needs of a particular application. It is envisioned that a particularly useful arrangement would include a segment that is at least primarily an adhesive component located adjacent to a segment that is at least primarily a hydrophilic component, which is, in turn, located adjacent to segment that is at least primarily an elastomeric component. The composite fiber may also include two or more components in a segment of fiber. The composition of each segment and number of segments may also vary over the length of the fiber. Additionally, the transition between segments may be either smooth or abrupt. Alternatively, the composition of the fiber may be constant over its length. The non-woven fiber assembly may also comprise a plurality of fibers wherein different fibers, individually or in combination, supply each component.

The method of making a non-woven fiber assembly, according to the present invention, includes the forming of at least one fiber, the at least one fiber containing an adhesive component, an elastomeric component, and a hydrophilic component. The at least one fiber may be formed by any technique that is compatible with each of the components of the fiber or fibers. It is envisioned that melt-blowing, the NGJ technique, and electrospinning are suitable methods for forming fibers according to the present invention. Electrospinning provides particular advantages. Fibers may also be formed by other techniques, including phase separation, casting in pores, and slitting of a film.

As discussed above, one of the major advantages of using electrostatically spun fibers in non-woven fiber assembly, is that these fibers can be produced having very small diameters, usually on the order of about 3 nanometers to about 3000 nanometers, and more preferably, on the order of about 10 nanometers to about 500 nanometers, and most preferably, on the order of about 10 nanometers to about 100 nanometers. Fibers formed by the NGJ technique also have very small diameters. Thus, given that these "nanofibers" can be formed into non-woven membranes of any desired shape and thickness relatively rapidly, their usefulness and desirability in medical dressings and other non-woven fiber assembly's can readily be appreciated.

When fibers having very small diameters are formed, a membrane with very small interstices and high surface area is produced. Non-woven fiber assemblies according to this invention, may be useful in medical dressings, diapers, feminine hygiene products, absorbent towels or wipes for the skin, and transdermal or oral delivery systems for therapeutic and prophylactic substances. It is also envisioned that the non-woven fiber assemblies may also be used for other purposes such as spill management, water transport and management in fuel cells, and for collecting and transporting water or other fluids from coalescence filters.

When the non-woven fiber assembly forms a medical dressing, the resultant medical dressing is microporous and breathable, but is resistant to high airflow. These are important and desirable characteristics of medical dressings. Generally, pores sizes for the medical dressing produced using such techniques range from about 50 nanometers to about 1 micron, small enough to protect the wound from bacterial penetration via aerosol particle capture mechanisms. Pore sizes in this range may also at least partially hinder the passage of viral particles through the dressing to the wound.

The non-woven mats or membranes of the present invention preferably have high surface areas of at least 5 $m^2/g$, and more preferably, approximately 100 $m^2/g$ for efficient fluid absorption and dermal delivery. The high surface areas may also impart high hemostatic potential for the dressing.

When used as a medical dressing, the non-woven fiber assembly of the present invention provides greater water vapor permeability, as expressed by water vapor flux, than commercial barrier films. In one embodiment, the electrospun membrane forms a medical dressing that has a water vapor flux at least ten fold greater than that of solid film barrier dressings. Preferably, the medical dressing provides at least 30-fold greater water vapor flux than a commercial barrier film. More preferably, the medical dressing provides at least 30-fold greater water vapor flux than a commercial barrier film.

The medical dressing is a thin but effective barrier to contaminants. The appropriate thickness of the fibers of the dressing depends on factors such as the fiber-forming materials used the diameter of the fibers, the structural arrangement of the fibers, the size of the pores formed by the fibers as well as the desired degree of air permeability and protection from contaminants. For example, the fibers may form a medical dressing when applied at a coating level of as little as about 0.1 $g/m^2$. The fibers may also be applied at a coating level of between about 0.1 and 100 $gm/m^2$. At one thickness, the fibers of the medical dressing provide greater than 97 percent filtration efficiency against aerosols between about 0.5 μm and about 20 μm in diameter. At another thickness, the fibers provide greater than 97 percent filtration efficiency against aerosols between about 0.1 μm and about 20 μm in diameter. The fibers may also be applied at a thickness which provides for substantially complete filtration of aerosols between about 0.5 and about 20 μm in diameter or even about 0.1 μm to about 20 μm in diameter.

While the medical dressing protects against contamination, it does so while allowing the passage of air. This allows penetration of oxygen through the dressing to a wound, burn, or other protected area, thereby permitting accelerated healing and a decreased likelihood of infection compared to wound dressings that do not permit airflow to the protected area. In one example, the medical dressing provides an airflow resistance of less than $5\times10^9\ m^{-1}$. Preferably, the medical dressing has an air flow resistance of less than $2\times10^8\ m^{-1}$. In another example, the medical dressing has an air flow resistance of less than $2\times10^7\ m^{-1}$.

The fibers and the resultant medical dressings and other non-woven fiber assemblies of the present invention are lightweight, oxygen and moisture permeable, yet protect against airborne contaminants such as dust, microbes, or other infectious agents. The ability of the membrane fibers to transport and deliver therapeutic additives to the site of a wound is also important. This ability to transport and deliver additives can be controlled through the choice of polymer carrier, density and thickness of the non-woven sheet of fibers, and/or layering of different membrane fiber compositions.

With respect to the fibers used in a medical dressing, it will be understood that the fibers may preferably be dry, and form strong membranes. However, in some instances, a wet fiber may be employed. Although wet fibers may be strong, wet fibers are generally softer and conform to the surface of the substrate to which they are applied better than dry fibers. Other advantages may include those set forth previously in discussion above of U.S. Pat. No. 4,043,331. In any event, the ability to form the fibers of the present invention directly onto the surface of a wound allows for improved flexibility in the composition of the fibers, improved porosity of the membrane, and improved strength, all in an inexpensive and timely manner. Moreover, the direct application of the fibers means that the fibers can be advantageously placed in intimate, and shape forming, contact with the total wound surface. This enables efficient removal of dead cells, fluid or bacteria from deep within the wound when the dressing is changed, thereby reducing or eliminating the need for debridement of the wound. Direct contact with the surface of the wound will also enable improved drug delivery to the wound. Finally, it will be appreciated that direct application provides for improved and, in fact, inherent, sterility of the fibers and, therefore, the dressing, thereby eliminating the need for gamma radiation or other treatments to disinfect the dressing materials. In addition, controlled generation of ozone and other active species may be used to assist with sterilization.

In one embodiment, the dressing also comprises a closed cell foam to protect the treated area against mechanical disturbance or to provide thermal insulation.

The non-woven fiber assembly of the present invention may include at least one fiber formed from a mixture of any of a variety of a hydrophilic polymers, elastomeric polymers, and polymers having adhesive properties. The fiber-forming material can be optionally blended with any of a number of medically important wound treatments, including analgesics and other pharmaceutical or therapeutic additives. Such polymeric materials suitable for electrospinning into fibers may include, for example, those inert polymeric substances that are absorbable and/or biodegradable, that react well with selected organic or aqueous solvents, or that dry quickly. Essentially any organic or aqueous soluble polymer or any dispersions of such polymer with a soluble or insoluble additive suitable for topical therapeutic treatment of a wound may be employed. When used in applications other than medical dressings, other additives may be used. For example, in spill management applications, particles useful for absorbing a particular type of compound may be encapsulated in one of the polymer components. For example, a non-woven fiber assembly that is useful for managing spills of hydrophobic compounds may have a compound that absorbs hydrophobic compounds encapsulated within one of the polymeric components of the assembly.

The dressing of the present invention may include a mixture of nanofibers that are elastomeric and either hydrophilic, or hydrophobic with hydrophilic particles attached. For example, WATERLOCK polymer (Grain Processing Corp., Muscatine, Iowa) can be incorporated into a highly hydrophilic bandage that can hold up to 60 times its dry weight of water or more. Such an elastomeric, water-containing wound dressing material may provide a reservoir of water, fluid flow driven by alternating compression and expansion of the bandage, transport of therapeutic substances to the wound and transport of soluble or water-transportable by-products of healing away from the wound.

It is envisioned that the proportion of each component in the non-woven fiber assembly may vary according to the particular requirements of a specific type of use. It is also envisioned that the proportion of each component in the dressing may vary within the non-woven fiber assembly itself such that the composition of the assembly on one surface differs from the composition of the assembly on another surface. For example, one or more fibers made primarily of an elastomeric polymer may form a surface of the dressing furthest from a wound. The percentage of elastomeric polymer present in fiber in this portion of the dressing may approach and include 100 percent. In the interior of the dressing, fiber with an increasing amount of a hydrophilic polymer may be present. The percentage of hydrophilic polymer present in fiber in this portion of the dressing may approach and include 100 percent. The thickness of this portion of the dressing may also vary according to the anticipated needs of a particular application. The fiber on the surface of the dressing to be placed in contact with the patient may contain an increasing amount of polymer having adhesive properties. The percentage of adhesive polymer used in fiber in this portion of the dressing will vary with the need for aggressive or non-aggressive adhesion, but may approach and include 100 percent. The transition from one type of polymer to another may be gradual, producing no distinct layers of fiber type within the dressing, or the transition may be abrupt, thereby producing distinct layers within the dressing. The polymer fiber may be applied in a sterile condition. Alternatively, the composition of the at least one fiber may be constant along the length of the fiber.

As described more fully below, the hydrophilic component, when contacted with water, is believed to absorb the water and to expand, thereby surrounding the adhesive component, keeping the adhesive from adhering to the surface of the wound. The hydrophilic component also keeps the dressing moist, facilitates movement of water to the external surface of the dressing, and facilitates the movement of therapeutic substances throughout the dressing. Examples of suitable hydrophilic polymers include, but are not limited to, linear poly(ethylenimine), cellulose acetate and other grafted cellulosics, poly(hydroxyethylmethacrylate), poly(ethyleneoxide), poly vinylpyrrolidone, polyurethanes, polypropyleneoxides and mixtures and co-polymers thereof. The hydrophilic component may also be a water absorbing gel such as WATERLOCK polymer or carboxymethyl cellulose. The hydrophilic component may be incorporated into the fiber, attached to the surface of the fiber, or physically held between fibers.

The elastomeric component of the present invention provides mechanical strength to the dressing and that ability to conform to stretching of the skin. Mechanical strength is needed not only to hold the assembly in place during use, but also to facilitate removal of the dressing when it needs to be changed. Examples of suitable elastomeric polymers include polyurethanes, polyesters, polyanhydrides, polyamides, polyimides and mixtures and co-polymers thereof.

Adhesive components are needed to adhere the assembly to a substrate. Suitable polymers having adhesive properties include homo-polymers and co-polymers of acrylates, polyvinylpyrrollidones, and silicones and mixtures thereof. The adhesive may be a fiber that forms an open network, attaching the dressing to the wound at many points, but allowing essential passage of fluids through interstices in the adhesive network.

The polymers contained in the fiber may also contribute to more than one component category. For example, an acrylate-block co-polymer may be used. In such a case, the acrylate block contributes adhesive properties while the co-polymer block contributes hydrophilic properties.

While not wishing to condition patentability on any particular mechanism of action, it is believed that the components of the fiber-forming polymers create structures internal to the fibers by phase separation that are in the form of rods, particles, sheets or other geometrical forms. It is also believed that upon wetting, the hydrophilic component may swell and expand in a way that physically prevents the adhesive component from coming in contact with a substrate surface. Thereby, a medical dressing of the present invention will adhere to undamaged skin, because the hydrophilic polymer has not been contacted by water and has not swollen to surround the adhesive component. The dressing will not adhere to a wound or tissue at an early stage of healing, on the other hand, because moisture from the wound contacts the hydrophilic component causing it to swell and interfere with the adherence of the adhesive to the wound.

In the same way, deliberate wetting of a part of the dressing that would otherwise adhere to the skin will cause the hydrophilic regions to swell. Such wetting and swelling makes the bandage easy to remove. Preferably, inadvertent wetting is avoided to keep the bandage in place.

The non-woven fiber assembly may also be used for other applications. For example, the fiber assembly may be utilized to deliver pesticides, nutrients or other desired compounds to crops. The fiber assembly would adhere to the crops when dry, but could be readily removed by washing with water. The assembly may also be used as a type of sponge or wall-less flask to absorb or contain water or other liquids. The fiber assembly would therefore be useful in diapers, personal hygiene products, absorbent towels and the like.

The present invention also provides a method of making a non-woven fiber assembly, the method comprising the steps of providing at least one fiber-forming material containing an adhesive component, an elastomeric component, and a hydrophilic component, and forming at least one fiber from the fiber-forming material. The fiber assembly of the present invention may be formed from soluble polymers in either organic or aqueous solvents. The fiber-forming material may be provided in a solvent such as an alcohol, ethyl acetate, acetone, or tetrahydrofuran (THF), for example. It may be desired in some applications that the solvent be biologically compatible.

The method may optionally include a treatment step following formation of the fibers to provide a desired property to the dressing. For example, fiber containing a water-soluble material may be cross-linked to form water-insoluble fibers. In another example, the fiber may be treated to include a therapeutic or pharmaceutical product. Linear polyethylenimine may be treated with nitric oxide to form linear polyethylenimine diazeniumdiolate, for example.

As mentioned above, the relative amounts of the adhesive component, the elastomeric component, and the hydrophilic component may vary over time during fiber formation, producing a medical dressing or other non-woven fiber assembly in which the composition at a first surface differs from the composition at a second surface. For example, one or more fibers may be electrospun primarily from an elastomeric polymer to form a surface of a medical dressing that will not contact the patient. As fiber is electro-spun to form the interior of the dressing, an increasing amount of a hydrophilic polymer is used to form the fiber. After a sufficient amount of fiber containing hydrophilic polymer is incorporated into the dressing, an increasing amount of polymer having adhesive properties is used to form the fiber of the dressing. The transition from one type of polymer to another may be gradual (i.e.—a constant gradient between polymer types), producing no distinct layers of fiber type within the dressing, or the transition may be abrupt (a step gradient between polymer types), thereby producing distinct layers within the dressing. The transition between regions of the dressing may also be the result of a non-constant or "skewed" gradient between polymer types. Other variations or combinations of transitions may be used in this method. Also, the layers in the center of the dressing may differ from those in other parts of the bandage by controlling the position of the fiber jet with an electric field or air currents, for example.

In one particular embodiment, a medical dressing is made according to the following method. At least one fiber is electrospun from an elastomeric polymer, such as elastomeric polyurethane, under conditions that produce a wet fiber, that is, a fiber containing excess solvent, either within the entirety of the fiber or only on the surface of the fiber. The wet fiber or fibers are collected on a receiver such as a non-stick film. The collected wet fiber will melt or fuse at places of intersection without sintering at high temperatures, to form a fibrous film with high water vapor transmission rate and air permeability. The conditions for electrospinning are then changed such that a dry fiber is received over the wet fiber. This may be accomplished, for example, by increasing the distance between the electrospinning device and the receiver. When a layer of dry fiber is laid down on the wet fiber, the composition of the polymer is changed to a hydrophilic polymer, such as a hydrophilic polyurethane. This second polymer may be introduced by a step gradient, a constant gradient, or a skewed gradient between polymer types. The concentration of hydrophilic polymer may approach or equal 100 percent. A predetermined amount of fiber is deposited and the composition of the polymer is then changed to an adhesive polymer. As with the previous transition between polymer types, the transition may occur via a step gradient, a constant gradient, or a skewed gradient between polymer types. The composition of this portion of the dressing may approach or equal 100 percent adhesive polymer. The adhesive polymer forms the surface of the dressing that is applied to the patient.

The present invention likewise provides a method of treating a patient comprising applying a medical dressing to a predetermined area of a patient, wherein the dressing contains one or more fibers and contains an adhesive component, an elastomeric component, and a hydrophilic component. This method may be used to apply one or more fibers to a burn, a wound or another area needing protection from contamination or an area requiring treatment with therapeutic or pharmaceutical compounds. The method may include forming the at least one fiber on a separate receiver and then transferring the at least one fiber to the predetermined area of the patient, or applying the at least one fiber directly onto the predetermined area.

As suggested hereinabove, other additives, either soluble additives or insoluble particulates, may also be included in the liquid(s) to be formed into the at least one fiber. Preferably, these additives are medically important topical additives provided in at least therapeutically effective amounts for the treatment of the patient. Such amounts depend greatly on the type of additive and the physical characteristics of the wound as well as the patient. Generally, however, such additives can be incorporated in the fiber in amounts ranging from trace amounts (less than 0.1 parts by weight per 100 parts polymer) to 500 parts by weight per 100 parts polymer, or more. Examples of such therapeutic additives include, but are not limited to, antimicrobial additives such as silver-containing antimicrobial agents, and antimicrobial polypeptides, analgesics such as lidocaine, soluble or insoluble antibiotics such as neomycin, thrombogenic compounds, nitric oxide releasing compounds that promote wound healing such as sydnonimines and diazeniumdiolates, bacteriocidal compounds, fungicidal compounds, anti-viral compounds, bacteriostatic compounds, anti-inflammatory compounds, anti-helminthic compounds, anti-arrhythmic compounds, antidepressants, antidiabetics, antiepileptics, antimuscarinics, antimycobacterial compounds, antineoplastic compounds, immunosuppressants, anxiolytic sedatives, astringents, beta-adrenoceptor blocking compounds, corticosteroids, cough suppressants, diagnostic compounds, diuretics, antiparkinsonian compounds, immunological compounds, muscle relaxants, vasodialators, hormones including steroids, parasympathomimetic compounds, radiopharmaceuticals, antihistamines and other antiallergic compounds, anti-inflammatory compounds such as PDE IV inhibitors, neurohormone inhibitors such as NK3 inhibitors, stress protein inhibitors such as p38/NK/CSBP/mHOG1 inhibitors, antipsychotics, and xanthines, adhesives, fragrances, odor absorbing compounds, and nucleic acids such as deoxyribonucleic acid, ribonucleic acid, and nucleotide analogs, enzymes and other proteins and growth factors.

In still another embodiment, additives that contribute to the structural properties of the article may be included in the medical dressing. These include small solid particles, dispersed droplets of immiscible liquids in which other substances may be dissolved, crosslinking compounds, blowing agents to create foams, adhesives, elastomers and the like, which may be chosen for their function in protecting and healing the wound.

It will be appreciated that a number of different types of membranes may be produced according to the present invention, depending upon how the fibers are produced and deposited. In one embodiment, the liquid to be formed into fiber is a mixture of an adhesive polymer, a hydrophilic polymer, and an elastomeric polymer. Thus, one fluid could provide the entire membrane. However, it is also envisioned that composite fibers of different compositions could be spun together or in sequential layers to provide a suitable membrane.

The method of using the medical dressing of the present invention may comprise applying at least one fiber to a wound or other area needing protection from contamination, or an area requiring treatment with therapeutic or pharmaceutical compounds, to form a fibrous non-woven matrix, wherein the dressing comprises a hydrophilic component, an elastomeric component and an adhesive component.

In another embodiment, the dressing additionally comprises at least one pharmaceutical or therapeutical agent selected from the group consisting of antibiotic compounds such as bacteriocidal and fungicidal compounds, bacteriostatic compounds, crosslinking compounds, analgesic compounds, thrombogenic compounds, nitric oxide releasing compounds such as sydnonimines and diazeniumdiolates that promote wound healing, other pharmaceutical compounds, adhesives, fragrances, odor absorbing compounds, and nucleic acids, without regard to solubility in a biocompatible solvent. In contrast to previous electrospun fibers, the additives are not limited to those that are soluble in the polymer/solvent combination. It has been discovered that even insoluble additives that may be added to the polymer/solvent combination of the present invention remain within the fiber.

Finally, the present invention also provides an apparatus for forming at least one composite fiber, the fiber comprising a hydrophilic component, an elastomeric component and an adhesive component. The apparatus comprises a plurality of reservoirs for containing more than one type of fiber-forming material, a plurality of valves each independently in communication with a reservoir, and a fiber-forming device selected from the group consisting of a spinnerette, a NGJ nozzle, and an electrospinning device, in communication with said valves.

An embodiment of the apparatus of the present invention may be described with reference to the figure. Apparatus 10 comprises a first reservoir 12, a second reservoir 16 and a third reservoir 20. First reservoir 12 is in fluid communication with a first valve 14. Likewise, second reservoir 16 is in fluid communication with a second valve 18 and third reservoir 20 is in fluid communication with a third valve 22. First, second, and third valves 14, 18, and 22 may be manually controlled or they may be placed in communication with a controller 24 for automated control. First, second, and third valves 14, 18, and 22 are optionally in communication with a mixing chamber 26, which is, in turn, in communication with a fiber-forming device 28. Alternatively, a spinning device (spinnerette, NGJ nozzle, electrospinning apparatus) may be attached to each reservoir. The rate of fiber production from each device may be regulated to supply the particular polymer in the amount needed to produce the desired spatially variable structure. When the fiber-forming device is an electrospinning device, a power source is in electrical communication with the electrospinning device.

Apparatus 10 may be used to form fibers according to the present invention by placing an adhesive component, an elastomeric component, and a hydrophilic component in each of the reservoirs 12, 16, and 20. The relative amounts of each component fed to fiber forming device 28 is controlled by selectively opening or closing each of valves 14, 18, and 22. The relative amounts of each component controls the composition of the fibers produced by fiber-forming device 28.

Figure 2:
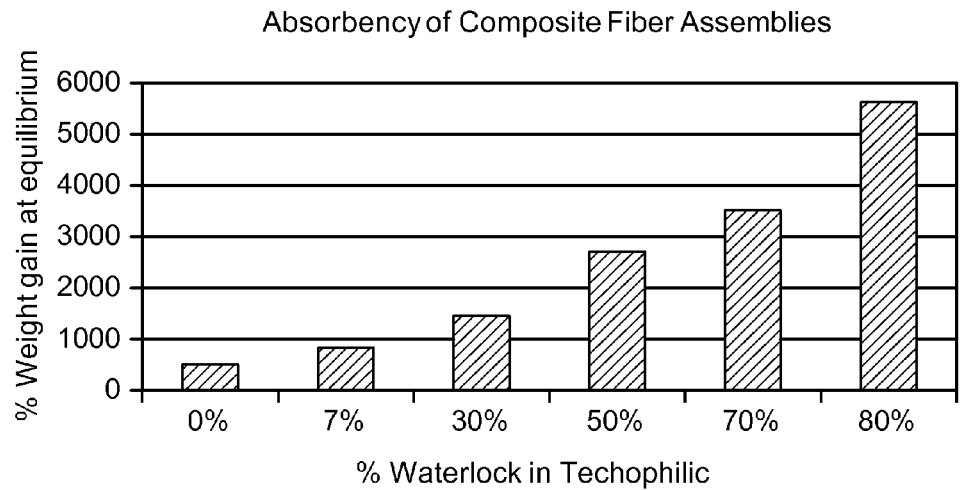
FIG. 2 is a graph showing the absorbency of nanofiber assemblies of the present invention.

In order to demonstrate the practice of the present invention, composite fibers were electrospun from a THF:ethanol solution (30:70) containing WATERLOCK A-180 and TECOPHILIC polymers to form non-woven fiber assemblies or mats. WATERLOCK polymers are corn starch/acrylamide/sodium acrylate copolymers available from Grain Processing Corp. (Muscatine, Iowa). WATERLOCK polymers contribute a hydrophilic component to the resulting fiber assembly. TECOPHILIC is an aliphatic polyether-based polyurethane available from Thermedics Polymer Products (Wilmington, Mass.), which contributes an elastomeric component and a hydrophilic component to the fiber assembly. Mats of fibers containing 7, 30, 50, 70, or 85 percent WATERLOCK (WL) were tested for their absorbency against the absorbency of a mat containing fibers with no WATERLOCK. The equilibrium water content was determined by soaking the fiber mats in distilled water for 24 hours at room temperature and comparing the weight of the mat before and after soaking. The percentage of weight gain for each sample is shown graphically in FIG. 2. FIG. 2 shows that addition of WATERLOCK polymer greatly increases the absorbency of the resulting fiber assembly.

Figure 3:
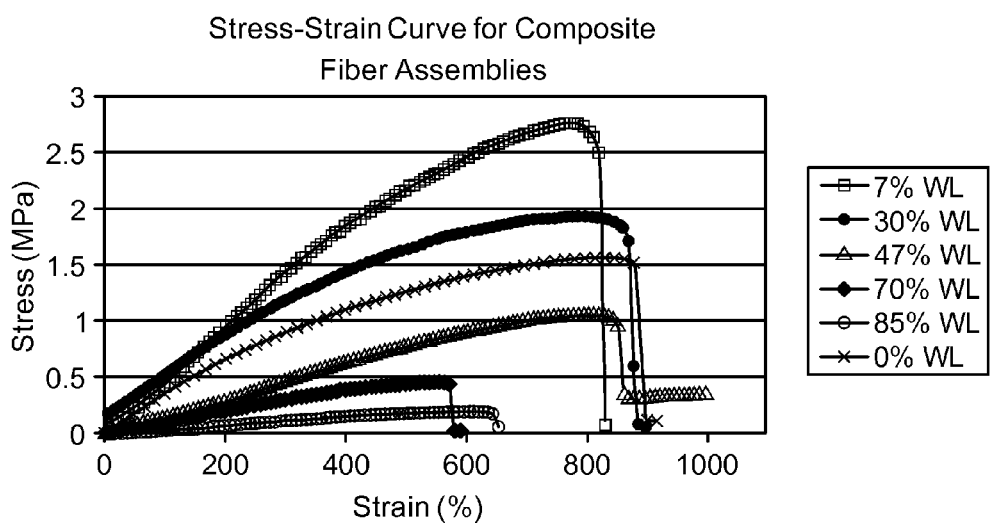
FIG. 3 is a stress-strain curve for nanofiber assemblies of the present invention.

Samples containing WATERLOCK and TECOPHILIC polymers were also tested for their stress-strain behavior. The samples were tested on an Instron fatigue test system model 5567 (Canton, Mass.) using an ASTM 638 pattern. The samples were stretched at a rate of 50 mm/min. The stress-strain behavior of samples containing 7, 30, 50, 70, or 85 percent WATERLOCK (WL) is shown in FIG. 3. According to these data, the amount of deformation (strain) that the samples could absorb exceeded 500% in each case. The tensile strength of the fiber assembly was greatest with 7 percent WATERLOCK, which was also greater than the sample consisting of TECOPHILIC polymer (0% WL).

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention pertains.

Based upon the foregoing disclosure, it should now be apparent that the medical dressing of the present invention will carry out the objects set forth hereinabove. It is, therefore, to be understood that any variations evident fall within the scope of the claimed invention and thus, the selection of specific component elements can be determined without departing from the spirit of the invention herein disclosed and described.

We claim:

1. A non-woven fiber assembly comprising one or more fibers wherein each fiber contains:
   a hydrophilic component selected from the group consisting of linear poly(ethyleneimine), cellulose acetate; grafted cellulosics; poly(hydroxyethylmethaacrylate, poly(ethyleneoxide), polyvinylpyrrolidone, polypropyleneoxides, mixtures and co-polymers thereof, carboxymethyl cellulose and water absorbing gel; and
   an elastomeric component selected from the group consisting of polyurethanes, polyesters, polyanhydrides, polyamides, polyimides, and mixtures and co-polymers thereof, and wherein the non-woven fiber assembly further comprises an adhesive component.

2. The non-woven fiber assembly of claim 1, wherein the assembly forms a component of a medical dressing.

3. The non-woven fiber assembly of claim 1, wherein the adhesive component is selected from homo- and co-polymers of acrylates, silicones, polyvinylpyrrolidones, and mixtures thereof.

4. The non-woven fiber assembly of claim 1, wherein the at least one fiber has a diameter of between about 3 nanometers and about 3000 nanometers.

5. The non-woven assembly of claim 1, wherein the adhesive component is located on, or in proximity to, the one or more fibers.

6. A method of treating a patient comprising: applying a non-woven fiber assembly of claim 1 to a predetermined area of the patient.

7. A method of making a non-woven fiber assembly, the method comprising the steps of:
   providing at least one fiber-forming material; forming at least one fiber from the at least one fiber-forming material, and producing a non-woven fiber assembly from the at least one fiber, wherein the at least one fiber forming material comprises a hydrophilic component selected from the group consisting of linear poly(ethyleneimine), cellulose acetate; grafted cellulosics; poly(hydroxyethylmethaacrylate, poly(ethyleneoxide), polyvinylpyrrolidone, polypropyleneoxides, mixtures and co-polymers thereof, carboxymethyl cellulose and water absorbing gel, an elastomeric component selected from the group consisting of polyurethanes, polyesters, polyanhydrides, polyamides, polyimides, and mixtures and co-polymers thereof, and optionally an adhesive component, and wherein each fiber contains a hydrophilic component and an elastomeric component, and optionally contains an adhesive component.

8. The method of claim 7, wherein the relative amounts of the adhesive component, the elastomeric component, and the hydrophilic component varies over time, thereby producing a fiber assembly in which the composition of the one or more fibers at a first surface of a dressing differs from the composition of the one or more fibers at a second surface of the dressing.

9. A non-woven fiber assembly comprising one or more fibers wherein each fiber contains:
   a hydrophilic component selected from the group consisting of linear poly(ethyleneimine), cellulose acetate; grafted cellulosics; poly(hydroxyethylmethaacrylate, poly(ethyleneoxide), polyvinylpyrrolidone, polyurethanes, polypropyleneoxides, mixtures and co-polymers thereof, carboxymethyl cellulose and water absorbing gel; and
   an elastomeric component selected from the group consisting of polyesters, polyanhydrides, polyamides, polyimides, and mixtures and co-polymers thereof, and wherein the non-woven fiber assembly further comprises an adhesive component.

10. The non-woven fiber assembly of claim 9, wherein the assembly forms a component of a medical dressing.

11. The non-woven fiber assembly of claim 9, wherein the adhesive component is selected from homo- and co-polymers of acrylates, silicones, polyvinylpyrrolidones, and mixtures thereof.

12. The non-woven fiber assembly of claim 9, wherein the at least one fiber has a diameter of between about 3 nanometers and about 3000 nanometers.

13. The non-woven assembly of claim 9, wherein the adhesive component is located on, or in proximity to, the one or more fibers.

14. A method of treating a patient comprising: applying a non-woven fiber assembly of claim 9 to a predetermined area of the patient.

15. A method of making a non-woven fiber assembly, the method comprising the steps of:
   providing at least one fiber-forming material; forming at least one fiber from the at least one fiber-forming material, and producing a non-woven fiber assembly from the at least one fiber, wherein the at least one fiber forming material comprises a hydrophilic component selected from the group consisting of linear poly(ethyleneimine), cellulose acetate; grafted cellulosics; poly(hydroxyethylmethaacrylate, poly(ethyleneoxide), polyvinylpyrrolidone, polyurethanes, polypropyleneoxides, mixtures and co-polymers thereof, carboxymethyl cellulose and water absorbing gel, an elastomeric component selected from the group consisting of polyesters, polyanhydrides, polyamides, polyimides, and mixtures and co-polymers thereof, and an adhesive component, and wherein each fiber contains a hydrophilic component and an elastomeric component, and contains an adhesive component.

16. The method of claim 15, wherein the relative amounts of the adhesive component, the elastomeric component, and the hydrophilic component varies over time, thereby producing a fiber assembly in which the composition of the one or more fibers at a first surface of a dressing differs from the composition of the one or more fibers at a second surface of the dressing.

* * * * *